United States Patent
Wu et al.

(10) Patent No.: US 12,359,979 B2
(45) Date of Patent: Jul. 15, 2025

(54) ORGANISM DETECTION APPARATUS

(71) Applicant: Wistron Corporation, New Taipei (TW)

(72) Inventors: Huan-Chun Wu, New Taipei (TW); Yao-Tsung Chang, New Taipei (TW)

(73) Assignee: Wistron Corporation, New Taipei (TW)

( * ) Notice: Subject to any disclaimer, the term of this patent is extended or adjusted under 35 U.S.C. 154(b) by 929 days.

(21) Appl. No.: 17/319,071

(22) Filed: May 12, 2021

(65) Prior Publication Data

US 2022/0205844 A1 Jun. 30, 2022

(30) Foreign Application Priority Data

Dec. 24, 2020 (TW) .................................. 109145895

(51) Int. Cl.
*G01K 1/02* (2021.01)
*B01L 3/00* (2006.01)
*C12Q 1/686* (2018.01)
*G01K 1/024* (2021.01)
*G01K 1/14* (2021.01)
*G01K 1/16* (2006.01)
*G01N 21/64* (2006.01)

(52) U.S. Cl.
CPC ............ *G01K 1/026* (2013.01); *B01L 3/5082* (2013.01); *C12Q 1/686* (2013.01); *G01K 1/024* (2013.01); *G01K 1/14* (2013.01); *G01K 1/16* (2013.01); *G01N 21/6428* (2013.01); *B01L 2300/1838* (2013.01)

(58) Field of Classification Search
None
See application file for complete search history.

(56) References Cited

U.S. PATENT DOCUMENTS

| 10,569,273 B2 | 2/2020 | Gong et al. | |
|---|---|---|---|
| 2005/0282266 A1* | 12/2005 | Teng | B01L 7/52 435/303.1 |
| 2008/0212643 A1 | 9/2008 | McGahhey et al. | |

(Continued)

FOREIGN PATENT DOCUMENTS

| CN | 109562383 | 4/2019 | |
|---|---|---|---|
| WO | WO-2014115863 A1 * | 7/2014 | ............ B01L 7/5255 |

OTHER PUBLICATIONS

"Office Action of Taiwan Counterpart Application", issued on Mar. 8, 2022, p. 1-p. 11.

(Continued)

*Primary Examiner* — William H. Beisner
(74) *Attorney, Agent, or Firm* — JCIPRNET

(57) ABSTRACT

A detection apparatus configured for PCR testing includes a carrier structure and a temperature detection module. The carrier structure is configured to carry a test tube, and the test tube is configured for containing a reagent and a specimen. The temperature detection module is disposed on the carrier structure and includes a heat transfer medium and a temperature sensor. The heat capacity of the heat transfer medium is approximately equal to a preset value, so as to match heat capacity of the reagent. The temperature sensor is configured to sense a temperature of the heat transfer medium. In addition, a method for detecting a temperature of the detection apparatus is also provided.

6 Claims, 15 Drawing Sheets

(56) References Cited

U.S. PATENT DOCUMENTS

| | | |
|---|---|---|
| 2012/0015365 A1* | 1/2012 | Bodin .................. C12Q 1/6876 |
| | | 435/6.12 |
| 2012/0264203 A1 | 10/2012 | Dinges |
| 2019/0091694 A1 | 3/2019 | Gong et al. |
| 2019/0105656 A1 | 4/2019 | Gong et al. |
| 2019/0111435 A1 | 4/2019 | Gong et al. |
| 2019/0118184 A1 | 4/2019 | Gong et al. |
| 2019/0134639 A1 | 5/2019 | Gong et al. |
| 2020/0282401 A1 | 9/2020 | Gong et al. |

OTHER PUBLICATIONS

"Search Report of Europe Counterpart Application", issued on May 31, 2022, p. 1-p. 7.

* cited by examiner

| A first reagent medium, a specimen, a temperature detection module, and another temperature detection module are carried by a carrier structure, in which the specimen is located in the first reagent medium, the temperature detection module includes a heat transfer medium and the temperature sensor, and the another temperature detection module includes another heat transfer medium and another temperature sensor, and the heat capacity (a heat capacity preset value for detection) of the heat transfer medium is not equal to the heat capacity (another heat capacity preset value for detection) of the another heat transfer medium | ~ S1 |
|---|---|

↓

| A temperature of the corresponding heat transfer medium and another temperature of the another corresponding heat transfer medium are respectively sensed by the temperature sensor and the another temperature sensor | ~ S2 |
|---|---|

↓

| A temperature of the first reagent medium is obtained by calculation through interpolation or extrapolation according to the temperature of the heat transfer medium and the another temperature of the another heat transfer medium | ~ S3 |
|---|---|

FIG. 21

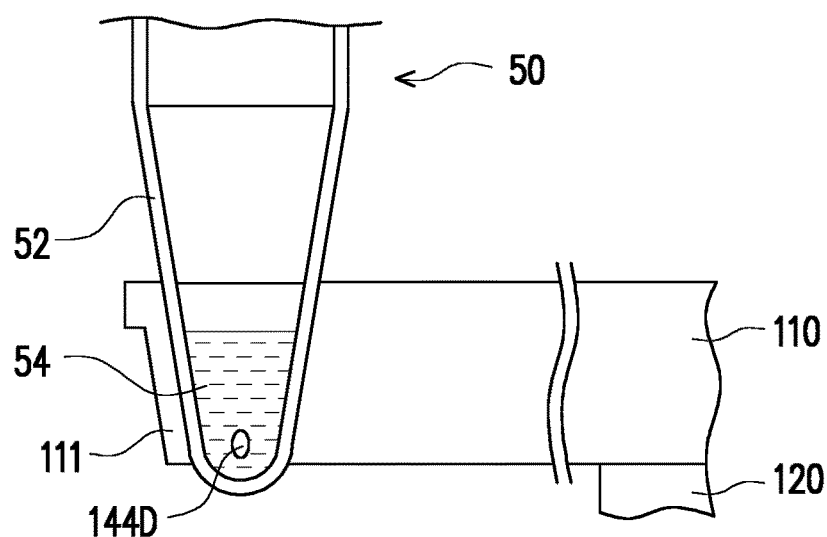

FIG. 22

ORGANISM DETECTION APPARATUS

CROSS-REFERENCE TO RELATED APPLICATION

This application claims the priority benefit of Taiwan application serial no. 109145895 filed on Dec. 24, 2020. The entirety of the above-mentioned patent application is hereby incorporated by reference herein and made a part of this specification.

BACKGROUND

Technical Field

The disclosure relates to a detection apparatus, and in particular to an organism detection apparatus.

Description of Related Art

Polymerase chain reaction (PCR) is a nucleic acid synthesis technology that uses the principle of deoxyribonucleic acid (DNA) replication to replicate specific deoxyribonucleic acid fragments in vitro. Through this technology, the quantity of nucleic acid analyte may be amplified to a large amount in a short period of time to enable amplification of a small quantity of the nucleic acid analyte in a specimen to a detectable quantity, so as to facilitate detection of the presence or absence of the nucleic acid analyte, and even determine its quantity. Therefore, the polymerase chain reaction technology is widely used in medical and biological laboratories, such as those specializing in biomedical testing and/or criminal forensics.

Multiple thermal cycles are performed during the process of quantitative polymerase chain reaction (qPCR) and the quantity of nucleic acid analyte doubles after each thermal cycle. The quantity of the analyte becomes 2 to the power of N times after N thermal cycles, and a light source of a specific wavelength and a sensor are required to detect the amplified quantity of the analyte after the specimen undergoes each thermal cycle. The thermal cycle may be as shown in FIG. 1, where in each cycle, DNA template of the analyte is first denatured by heating, after which primer annealing is performed by lowering the temperature, and then DNA synthesis of the analyte is performed by heating, which enables the doubling of the quantity of the analyte DNA. The next cycle is initiated with continuation of heating. For example, after 35 thermal cycles, the quantity of analyte may be amplified to 2 to the power of 35 times. In the process of thermal cycling, an excitation light source is required to irradiate the specimen so that the analyte emits fluorescence during synthesis, and an optical sensor is used to detect fluorescence intensity of the specimen to determine the quantity of the analyte at that moment, so as to achieve the goal of quantitative detection. In order to obtain the temperatures of the reagent and the specimen in the reagent for the control of the thermal cycling, the conventional technology embeds the temperature sensing element in a thermal conductive structure at a position closer to the test tube. However, the reagent is separated from the thermal conductive structure by the test tube, and the position, and/or thermal resistance, and/or specific heat between the reagent and the test tube, and between the test tube and the thermal conductive structure are different. As a result, the temperature sensing element in the thermal conductive structure is unable to accurately sense the temperature of the reagent during the thermal cycle in real time, and the variation of the temperature differences between the temperature sensed by the temperature sensing element and the real temperature of the reagent are non-linear, causing the actual temperature value of the reagent in the thermal cycle to be significantly different from the sensed temperature value, either in terms of the numerical value or of the trend of temperature increasing/decreasing, as shown in FIG. 2. Therefore, it is difficult to precisely control the thermal cycling.

SUMMARY

The disclosure provides an organism detection apparatus, which can accurately sense a temperature of the reagent and the specimen during a thermal cycle.

A detection apparatus of the disclosure, configured for polymerase chain reaction (PCR) testing, and includes a carrier structure and a temperature detection module. The temperature detection module is disposed on the carrier structure. The temperature detection module includes a heat transfer medium and a temperature sensor. A heat capacity of the heat transfer medium is approximately equal to a preset value for detection. The temperature sensor is disposed in the heat transfer medium and is configured to sense a temperature of the heat transfer medium.

In an embodiment of the disclosure, the detection apparatus further includes a test tube disposed on the carrier structure, and the heat transfer medium is accommodated in the test tube.

In an embodiment of the disclosure, the heat transfer medium is a reagent.

In an embodiment of the disclosure, the detection apparatus further includes a test tube disposed on the carrier structure, and a reagent, a specimen and the temperature sensor are accommodated in the test tube.

In an embodiment of the disclosure, the temperature detection module further includes a wireless signal processing unit, and the wireless signal processing unit is adapted to receive a wireless sensing signal from the temperature sensor.

In an embodiment of the disclosure, the heat transfer medium does not have the specimen.

In an embodiment of the disclosure, the test tube has an opening, and the temperature sensor is configured at the opening and protrudes into the test tube.

In an embodiment of the disclosure, the opening is located at a bottom end of another test tube.

In an embodiment of the disclosure, the heat transfer medium is a solid, and the solid is at least partially embedded in the carrier structure and wraps around the temperature sensor.

In an embodiment of the disclosure, a material of the solid material includes resin.

In an embodiment of the disclosure, the detection apparatus further includes a heat source. The carrier structure is a thermal conductive structure and is connected to the heat source. The temperature detection module includes a processing unit, and the processing unit is adapted to receive a sensing signal from the temperature sensor and is adapted to compensate a temperature sensed by the temperature sensor according to a temperature difference constant.

In an embodiment of the disclosure, the detection apparatus further includes a heat source. The carrier structure is a thermal conductive structure and is connected to the heat source. The carrier structure has multiple sockets and each of the sockets is adapted to carry the reagent to be tested. A distance between the heat source and the heat transfer medium is greater than a distance between the heat source and the socket.

In an embodiment of the disclosure, the detection apparatus further includes a test tube disposed on the carrier structure. The heat transfer medium includes a non-reagent material, and the non-reagent material is accommodated in the test tube. The temperature sensor is located in the test tube or on an outer side of the test tube.

In an embodiment of the disclosure, a heat capacity of the non-reagent material is equal to a preset value for detection.

In an embodiment of the disclosure, a material of the non-reagent material includes resin or water.

In an embodiment of the disclosure, the temperature sensor is located in the test tube, and the temperature detection module further includes a signal line. The signal line is connected to the temperature sensor, and the signal line extends from a bottom end or a top end of the test tube to an outer side of the test tube.

In an embodiment of the disclosure, the detection apparatus further includes a heat source. The carrier structure is a thermal conductive structure and is connected to the heat source. The temperature detection module includes a processing unit, and the processing unit is adapted to receive a sensing signal from the temperature sensor and is adapted to compensate a temperature sensed by the temperature sensor according to a temperature difference constant.

In an embodiment of the disclosure, the top end of the test tube of the heat transfer medium is flushed with a top end of the non-reagent material.

In an embodiment of the disclosure, the detection apparatus further includes a heat source and an optical sensing device. The carrier structure is a thermal conductive structure and is connected to the heat source, and the optical sensing device is adapted to sense a concentration of the specimen in the reagent.

A method for detecting a temperature of an organism specimen of the disclosure includes the following steps. A carrier structure is used to carry a first reagent medium, a specimen and at least two temperature detection modules. The specimen is located in the first reagent medium. Each of the temperature detection modules includes a heat transfer medium and a temperature sensor. A heat capacity of one of the heat transfer mediums is not equal to the heat capacity of the another heat transfer medium. A temperature of the corresponding heat transfer medium is sensed by each of the temperature sensors. A temperature of the first reagent medium is obtained according to the temperatures of the two heat transfer mediums.

In an embodiment of the disclosure, the detection apparatus further includes another temperature detection module disposed on the carrier structure. The another temperature detection module includes another heat transfer medium and another temperature sensor. A heat capacity of the another heat transfer medium is approximately equal to another preset value for detection. The another temperature sensor is disposed in the another heat transfer medium and configured to sense another temperature of the another heat transfer medium.

A detection apparatus of the disclosure, configured for PCR testing, and includes a carrier structure and a temperature detection module. The temperature detection module is disposed on the carrier structure. The temperature detection module includes a heat transfer medium and a temperature sensor. A heat capacity of the heat transfer medium is approximately equal to a heat capacity preset value for detection. The temperature sensor is disposed in the heat transfer medium and is configured to sense a temperature of the heat transfer medium.

In an embodiment of the disclosure, the detection apparatus further includes a holding tube disposed on the carrier structure, and the heat transfer medium is contained in the holding tube.

In an embodiment of the disclosure, the holding tube is a test tube.

In an embodiment of the disclosure, a material of the holding tube includes a test tube material.

In an embodiment of the disclosure, the temperature detection module further includes a signal line connected to the temperature sensor.

In an embodiment of the disclosure, the carrier structure further includes multiple sockets, and the heat transfer medium is disposed on the sockets.

In an embodiment of the disclosure, the carrier structure further includes an extension portion, and the heat transfer medium is disposed on the extension portion.

In an embodiment of the disclosure, the heat transfer medium is a reagent.

In an embodiment of the disclosure, the heat transfer medium does not generate a phase change within a working temperature range.

In an embodiment of the disclosure, the temperature detection module is a replaceable temperature detection module.

In an embodiment of the disclosure, the temperature detection module further includes a wireless signal processing unit, and the wireless signal processing unit is configured to receive a wireless sensing signal from the temperature sensor.

In an embodiment of the disclosure, the detection apparatus further includes another temperature detection module disposed on the carrier structure. The another temperature detection module includes another heat transfer medium and another temperature sensor. A heat capacity of the another heat transfer medium is approximately equal to another heat capacity preset value for detection. The another temperature sensor is disposed in the another heat transfer medium and configured to sense another temperature of the another heat transfer medium.

In an embodiment of the disclosure, the another heat capacity preset value for detection is equal to the heat capacity preset value for detection.

In an embodiment of the disclosure, the another heat capacity for detection preset value is not equal to the heat capacity preset value for detection.

A method for detecting a temperature of the disclosure includes the following steps. A carrier structure is disposed. A heat transfer medium is disposed on the carrier structure, and heat capacity of the heat transfer medium is equal to a heat capacity preset value for detection. A temperature sensor is disposed in the heat transfer medium. The temperature sensor is used to sense a temperature of the heat transfer medium.

In an embodiment of the disclosure, the heat transfer medium is a reagent.

In an embodiment of the disclosure, the method for detecting the temperature further includes providing a specimen in the reagent.

In an embodiment of the disclosure, the method for detecting the temperature further includes the following steps. Another heat transfer medium is disposed on the carrier structure, and the heat capacity of the another heat transfer medium is equal to another heat capacity preset value for detection. Another temperature sensor is disposed in the another heat transfer medium. The another temperature sensor is used to sense another temperature of the another heat transfer medium.

In an embodiment of the disclosure, the method for detecting the temperature further includes the following steps. A test tube is provided on the carrier structure. The test tube contains a reagent and a specimen, and a heat capacity of the reagent is equal to the heat capacity preset value for detection or the another heat capacity preset value for detection.

In an embodiment of the disclosure, the method for detecting the temperature further includes the following steps. A test tube is provided on the carrier structure. The test tube contains a reagent and a specimen, and a heat capacity of the reagent is not equal to the heat capacity preset value for detection or the another heat capacity preset value for detection.

In an embodiment of the disclosure, the method for detecting the temperature further includes performing compensation on a temperature sensed by the temperature sensor using a temperature difference constant.

In an embodiment of the disclosure, the heat transfer medium and the temperature sensor are disposed in a replaceable temperature detection module.

Based on the above, in the temperature detection module of the disclosure, the temperature sensor is used to measure the temperature of the heat transfer medium. The heat transfer medium may be the reagent itself, and as the temperature sensor directly measures the temperature of the reagent, the scenario in which the sensed temperature does not match the actual temperature will not occur. In addition, the heat transfer medium may be an additional medium whose heat capacity is the same as that of the reagent, thereby enabling the temperature detection module to sense the temperature of the heat transfer medium through the temperature sensor and accurately obtain the temperature of the reagent. In addition, the quantity of the temperature sensors may be at least two and respectively includes heat transfer mediums with different thermal capacities. Therefore, even if the heat capacity of the heat transfer medium is not equal to that of the reagent, the temperature of the reagent may still be estimated by interpolation or extrapolation according to the temperature s sensed by the temperature sensors of the two heat transfer mediums.

BRIEF DESCRIPTION OF THE DRAWINGS

FIG. 21 is a flowchart of a method for detecting a temperature of a specimen according to an embodiment of the disclosure.

FIG. 22 is a partial schematic view of a detection apparatus according to yet still another embodiment of the disclosure.

DESCRIPTION OF THE EMBODIMENTS

Figure 3:
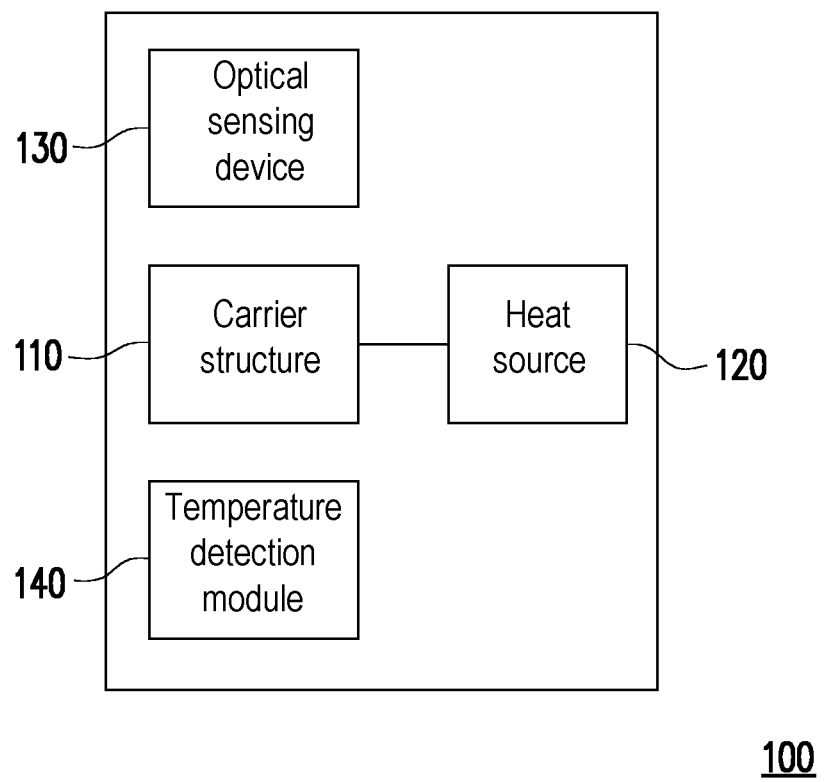
FIG. 3 is a schematic block diagram of a detection apparatus according to an embodiment of the disclosure.
Figure 4:
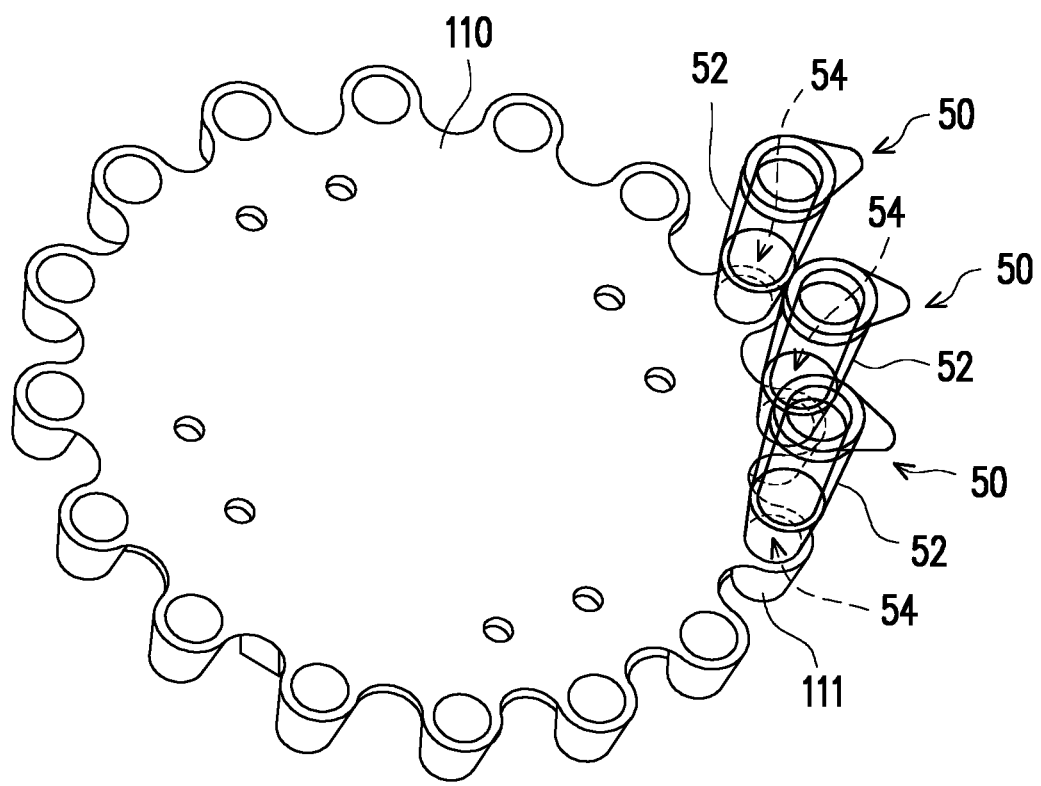
FIG. 4 is a perspective view of some of the components of the detection apparatus in FIG. 3.

FIG. 3 is a schematic block diagram of a detection apparatus according to an embodiment of the disclosure. FIG. 4 is a perspective view of some of the components of the detection apparatus in FIG. 3. With reference to FIGS. 3 and 4, a detection apparatus 100 of the embodiment is, for example, a polymerase chain reaction apparatus and includes a carrier structure 110, a heat source 120, an optical sensing device 130, and a temperature detection module 140. The carrier structure 110 has multiple sockets 111 adapted to carry multiple first reagent mediums 50 (although three are shown in FIG. 4, other suitable quantity is possible). Specifically, each of the first reagent mediums 50 includes a test tube 52 and a reagent 54 accommodated in the test tube 52, and a specimen is placed or dissolved in the reagent 54. The specimen is, for example, cells, tissues, organs, body fluids, etc., retrieved from an organism, and an actual analyte is, for example, an deoxyribonucleic acid in the specimen. The test tubes 52 have a same material and size specifications, and the reagents 54 have a same composition. For example, capacity of a commonly used test tube is 0.2 ml, and volume of the reagent is about 0.01 ml to 0.025 ml. However, the embodiments of the disclosure are not limited to these test tube capacities and reagent volumes, and the capacity of the test tube and the volume of the reagent may be larger or smaller. For example, the capacity of the test tube may be 0.25 ml or 0.15 ml, and the volume of the reagent may be about 0.030 ml or 0.008 ml.

Figure 1:
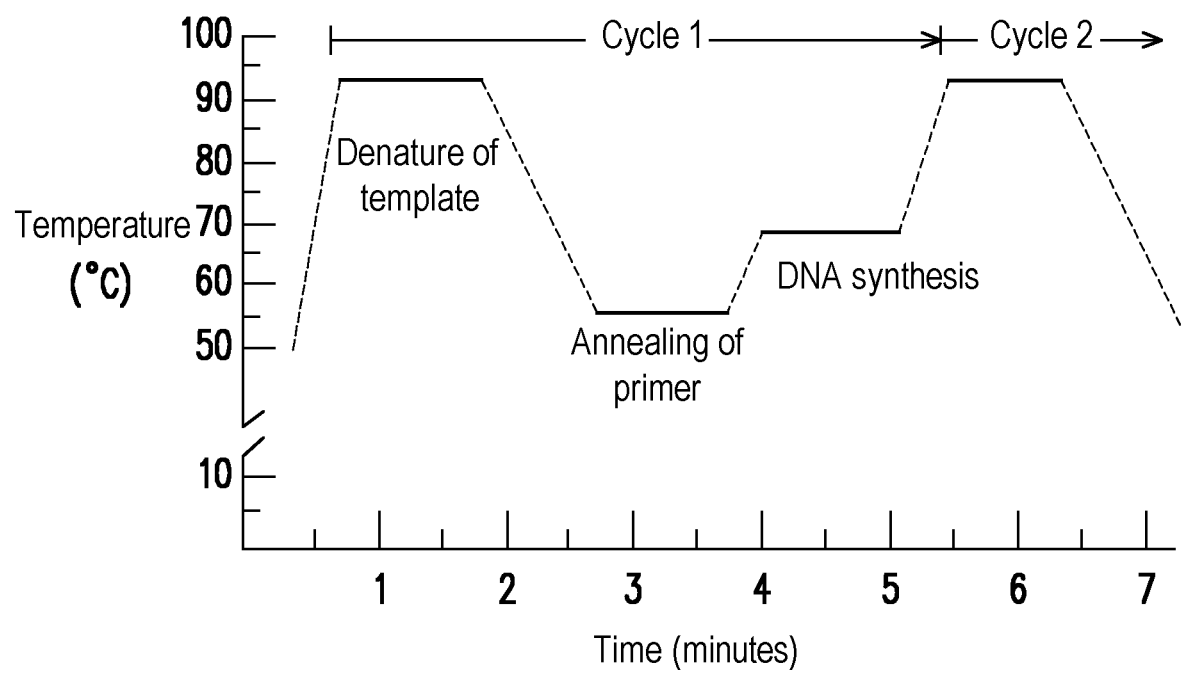
FIG. 1 shows a thermal cycle of a polymerase chain reaction.
Figure 2:
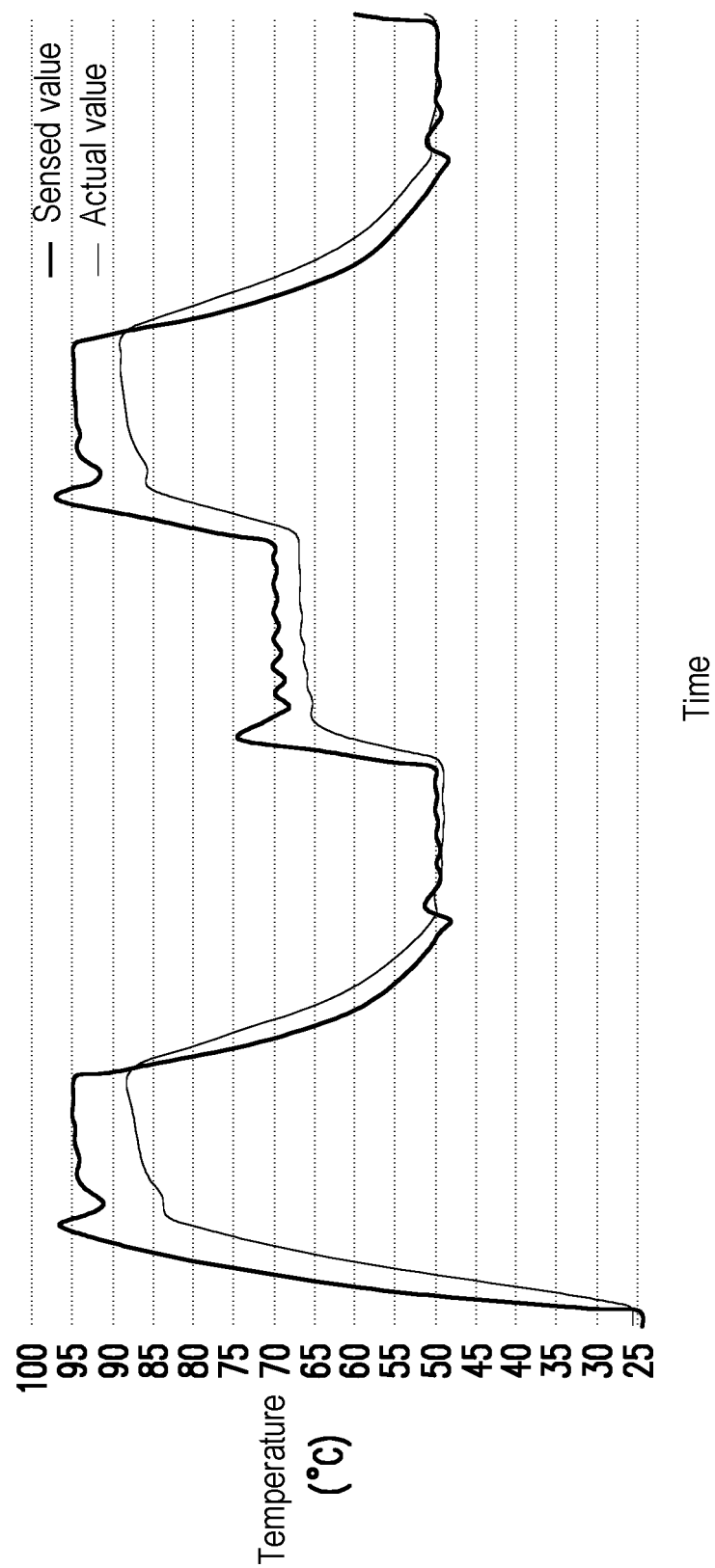
FIG. 2 shows actual and sensed temperature values of the reagent during the thermal cycle of a conventional polymerase chain reaction apparatus.

The carrier structure 110 is a thermal conductive structure and is connected to the heat source 120. According to an embodiment of the disclosure, the heat source 120 may be disposed above or below the carrier structure 110, inside the carrier structure 110, or at other positions thereof (not shown in FIG. 4). The test tube 52 is heated through the carrier structure 110, thereby heating the reagent 54 and the specimen, and enabling the reagent 54 and the specimen to be repeatedly subjected to thermal cycles as shown in FIG. 1, so as to amplify the quantity of the analyte through a polymerase chain reaction. The optical sensing device 130 is configured to sense the quantity of the analyte in the reagent 54. According to an embodiment of the disclosure, the optical sensing device 130 has an excitation light source and an optical sensor (not shown in FIG. 4). The excitation light source may emit light of a specific wavelength to irradiate the reagent 54, so as to enable the analyte to emit fluorescence during each of the thermal cycle. The optical sensor may detect fluorescence intensity of the specimen to determine the quantity of the analyte at the moment. The temperature detection module 140 is configured to sense a temperature in the detection apparatus 100 to facilitate the control of the thermal cycle. According to an embodiment of the disclosure, the optical sensing device 130 may include one or multiple types of excitation light sources and one or multiple types of optical sensors, which are configured for various corresponding reagents 54. According to an embodiment of the disclosure, the carrier structure 110 is a turntable, and may be rotated to enable each of the first reagent mediums 50 and the specimens therein to be irradiated by the excitation light source and to undergo optical detection. According to another embodiment of the disclosure, the detection apparatus 100 is, for example, a polymerase chain reaction apparatus and includes the carrier structure 110, the heat source 120, a non-optical sensing device 130' (not shown), and the temperature detection module 140, where the non-optical sensing device 130' is configured to sense the quantity of the analyte in the reagent 54.

A point of the disclosure is to enable a temperature sensed by a temperature sensor to be close to the temperature of the reagent 54 by adjusting an environment of the temperature sensor of the temperature detection module 140, thereby enabling temperature control to be more accurate. In some embodiments of the disclosure, the temperature detection module 140 is designed to have approximately the same thermal resistance as the first reagent medium 50 such that the influence of the thermal resistance on a temperature change may be ignored when the temperature detection module 140 is used to calculate the temperature of the reagent 54. In other embodiments of the disclosure, the temperature detection module 140 is designed to include an additional heat transfer medium, and heat capacities of the temperature detection module 140 and the reagent 54 are approximately the same, and therefore the rise in the temperature during absorption of the same heat is approximately the same, the influence of the heat capacity on the temperature change may be ignored when the temperature detection module 140 is used to calculate the temperature of the reagent 54. In some other embodiments of the disclosure, it is designed such that the thermal resistances of the temperature detection module 140 and the first reagent medium 50 are approximately the same, and the heat capacities of the temperature detection module 140 and the reagent 54 are approximately the same. Under such conditions, since influence due to the thermal resistance and the heat capacity are both very little and may be ignored, the temperature of the reagent 54 may be accurately obtained by using the temperature sensor to sense a temperature of the additional heat transfer medium. These will be described specifically below. The following embodiments correspond to the foregoing embodiments, therefore the same or similar elements are represented by the same or similar reference numerals.

Figure 5:
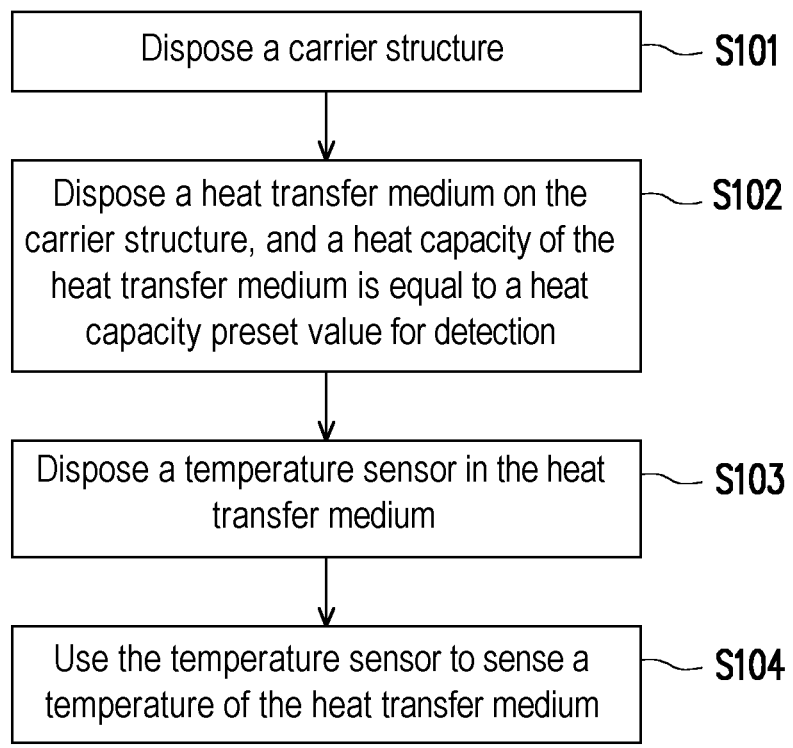
FIG. 5 is a flowchart of a method for detecting a temperature of a specimen according to an embodiment of the disclosure.

FIG. 5 is a flowchart of a method for detecting a temperature of a specimen according to an embodiment of the disclosure. With reference to FIG. 5, firstly, a carrier structure is disposed (Step S101). A heat transfer medium is disposed on the carrier structure, and a heat capacity of the heat transfer medium is equal to a heat capacity preset value for detection (Step S102). A temperature sensor is disposed in the heat transfer medium (Step S103). The temperature sensor is used to sense a temperature of the heat transfer medium (Step S104).

A detection apparatus corresponding to the method for detecting the temperature in FIG. 5 will be described more specifically by means of a figure/figures as follows.

Figure 6:
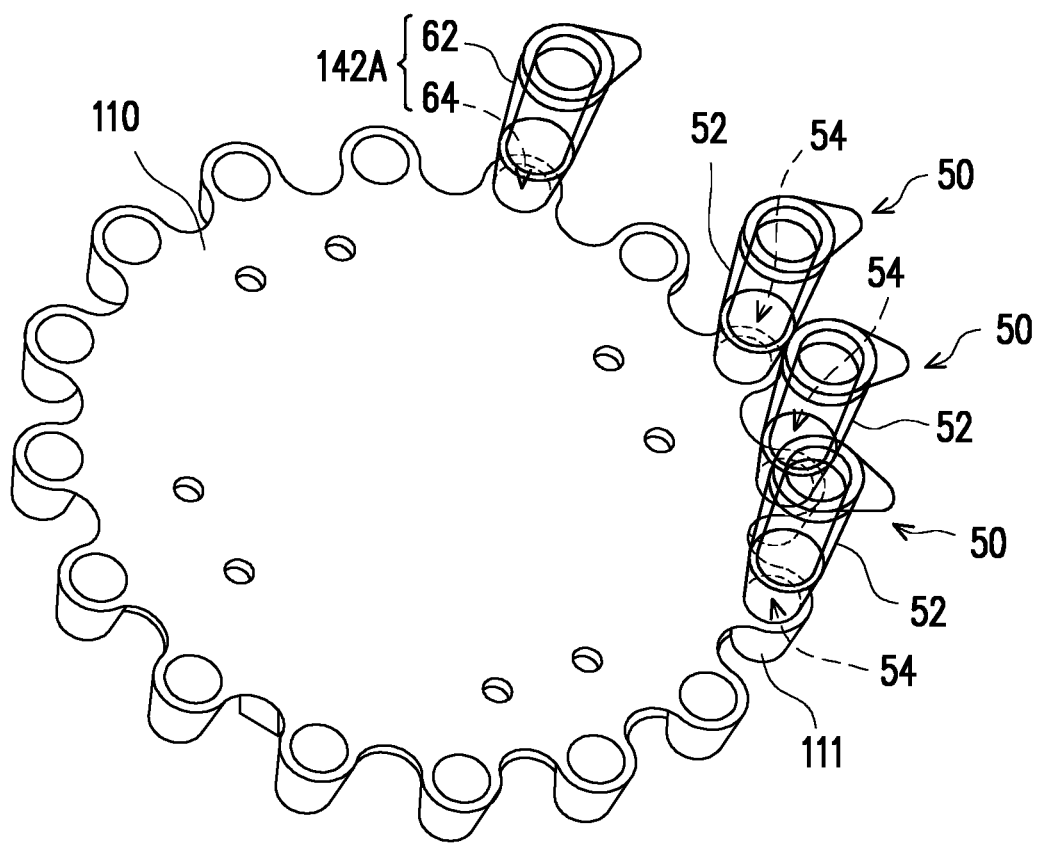
FIG. 6 shows an addition of a temperature sensing module to the detection apparatus in FIG. 4.
Figure 7:
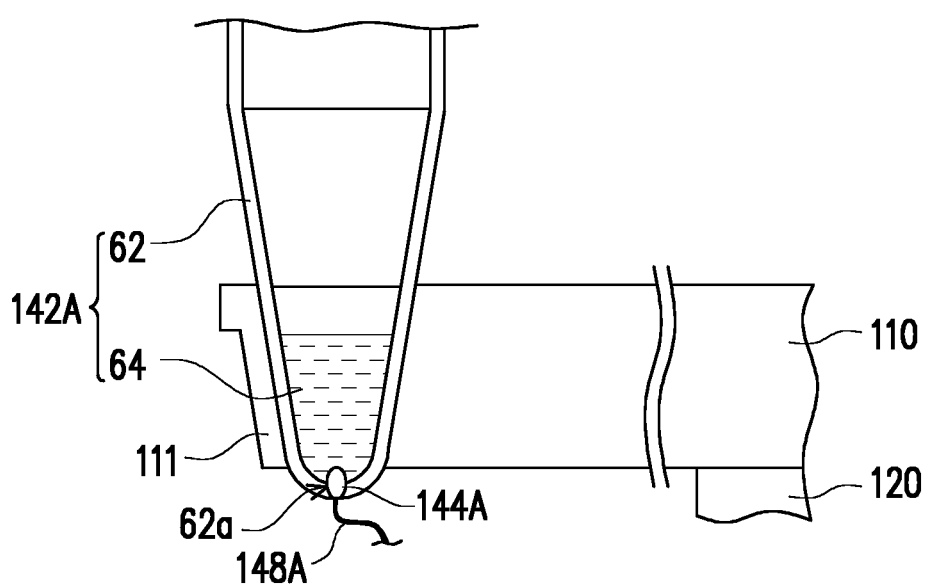
FIG. 7 shows some of the components of the temperature sensing module in FIG. 6.
Figure 8:
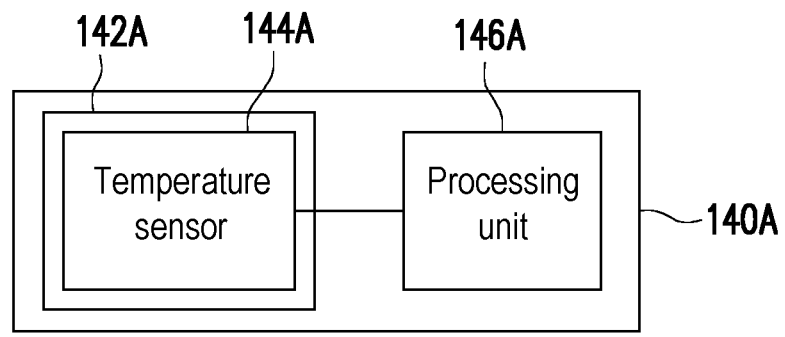
FIG. 8 is a schematic block diagram corresponding to the temperature sensing module in FIG. 7.

FIG. 6 shows an addition of a temperature sensing module to the detection apparatus in FIG. 4. FIG. 7 shows some of the components of the temperature sensing module in FIG. 6. FIG. 8 is a schematic block diagram corresponding to the temperature sensing module in FIG. 7. A temperature sensing module 140A shown in FIGS. 6 to 8 includes a second reagent medium 142A, a temperature sensor 144A, and a processing unit 146A. The second reagent medium 142A includes a test tube 62 and a heat transfer medium 64. The heat transfer medium 64 is an additionally disposed component configured to sense the temperature rather than an analyte. A heat capacity of the heat transfer medium 64 is set to be approximately equal to a heat capacity preset value for detection, and the heat capacity preset value for detection corresponds to a heat capacity of a reagent to be tested. Specifically, composition of the heat transfer medium 64 is the same as composition of the reagent 54, therefore specific heat is the same. Mass of the heat transfer medium 64 is approximately the same as mass of the reagent 54, therefore the heat capacity of the heat transfer medium 64 is approximately the same as the heat capacity of the reagent 54, as heat capacity=mass*specific heat. However, there is no specimen in the heat transfer medium 64, that is, only difference between the heat transfer medium 64 and the reagent 54 is presence or absence of the specimen. Since content of the specimen is negligible compared to the reagent, it has little influence on overall heat capacity of the reagent 54, therefore the influence of the presence or absence of the specimen on the temperature and the sensing of the temperature may be ignored. In this way, the temperature sensing module 140A may sense the temperature of the additionally disposed heat transfer medium 64 through the temperature sensor 144A to accurately obtain the temperature of the reagent 54. In addition, in the embodiment, since a material and size specifications of the test tube 62 are the same as the material and the size specifications of the test tube 52, the temperature measured by the temperature sensor 144A is further enabled to be close to the temperature of the reagent 54. In another embodiment, the test tubes 62 may be other types of holding tubes 62, and a material and/or size specifications may be different from those of the test tube 52. In other embodiments, the test tube 62 or the holding tube 62 has the same heat capacity and/or thermal resistance as the test tube 52, or a difference therebetween is small and has little influence on overall measurement of the temperature. The processing unit 146A is configured to receive a signal from the temperature sensor 144A and convert it into temperature information to obtain the temperature of the reagent 54 and the specimen.

With reference to FIG. 7, in the embodiment, a bottom end of the test tube 62 has an opening 62a. The temperature sensor 144A is configured at the opening 62a and protrudes into the test tube 62, and is connected to the processing unit 146A through a signal line 148A. Since the bottom end of the test tube 62 is not on a heat transfer path between the carrier structure 110 and the second reagent medium 142A, the opening 62a formed at the bottom end of the test tube 62 has little influence on heat conduction between the carrier structure 110 and the heat transfer medium 64 or the second reagent medium 142A and may be ignored. In other embodiments, the temperature sensor 144A may be configured to be accommodated in the test tube 62 by other appropriate manners, and the disclosure is not limited thereto. In addition, the signal line 148A shown in FIG. 7 is only for illustration, and it may be configured along the carrier structure 110 or embedded in the carrier structure 110, and the disclosure does not limit its configuration manner.

Figure 9:
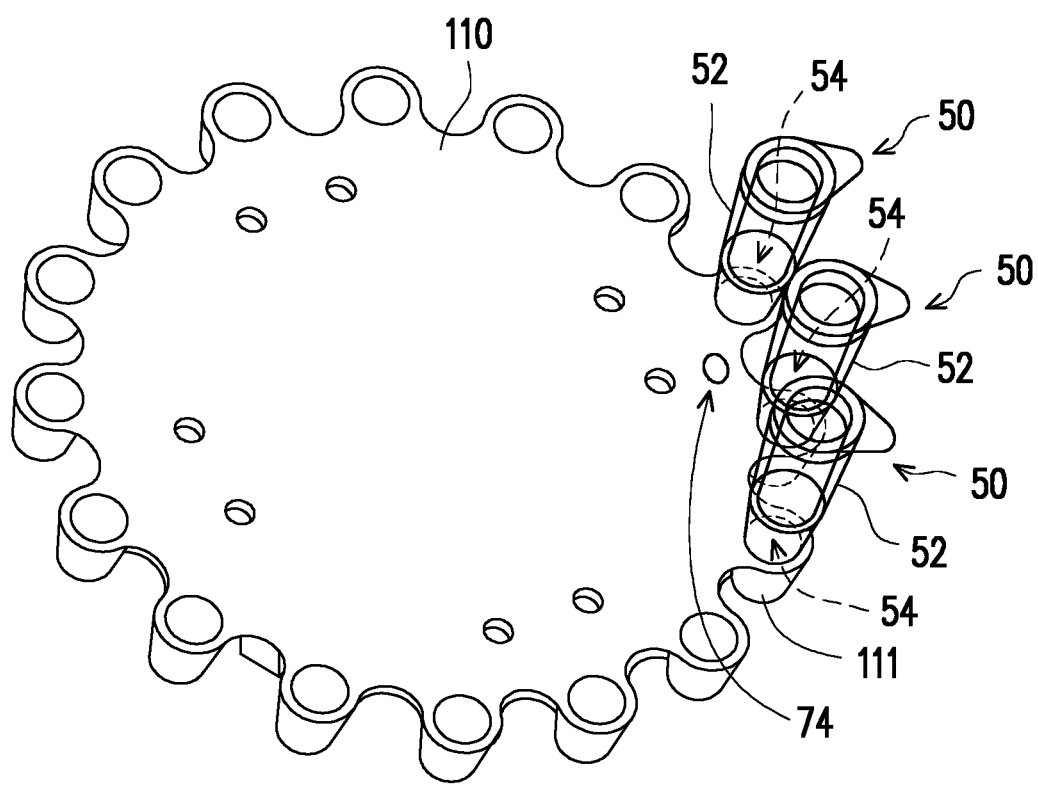
FIG. 9 is a perspective view of some of the components of a detection apparatus according to another embodiment of the disclosure.
Figure 10:
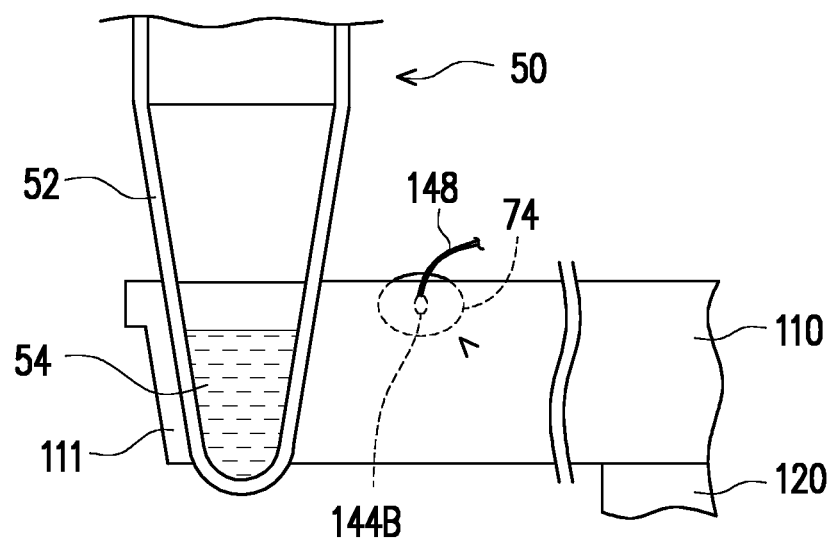
FIG. 10 shows some of the components of the temperature sensing module in FIG. 9.
Figure 11:
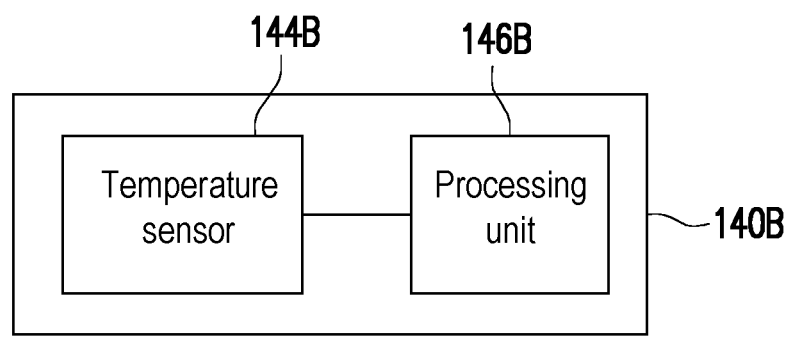
FIG. 11 is a schematic block diagram corresponding to the temperature sensing module in FIG. 10.

FIG. 9 is a perspective view of some of the components of a detection apparatus according to another embodiment of the disclosure. FIG. 10 shows some of the components of the temperature sensing module in FIG. 9. FIG. 11 is a schematic block diagram corresponding to the temperature sensing module in FIG. 10. A difference between the embodiment shown in FIGS. 9 to 11 and the embodiment shown in FIGS. 6 to 8 is that a disposition position of a heat transfer medium 74 shown in FIGS. 9 to 11 is not in the socket 111, instead it is near to the socket 111. A heat capacity of the heat transfer medium 74 is approximately equal to the heat capacity of the reagent 54. According to an embodiment of the disclosure, the heat transfer medium 74 is a non-reagent material, for example, resin (such as nylon or polystyrene). The heat transfer medium 74 is at least partially embedded in the carrier structure 110 and wraps around a temperature sensor 144B, and the temperature sensor 144B is connected to a processing unit 146B through a signal line 148B. According to another embodiment of the disclosure, the heat transfer medium 74 is almost completely embedded in the carrier structure 110. Since the thermal capacities of the heat transfer medium 74 and the reagent 54 are approximately equal, the temperature of the reagent 54 may be accurately obtained or the temperature of the reagent 54 is accurately calculated through sensing of the temperature of the heat transfer medium 74 by the temperature sensor 144B. Since heat capacity is equal to product of mass and specific heat, product of mass and specific heat of the heat transfer medium=product of mass and specific heat of the reagent when the heat capacity of the reagent is equal to the heat capacity of the heat transfer medium. At this time, although the specific heat of the heat transfer medium and the specific heat of the reagent may be different depending on different materials, the same heat capacity may be achieved as long as the mass of the heat transfer medium and the mass of the reagent are used as inverse ratio of the specific heat of the heat transfer medium and the specific heat of the reagent. According to an embodiment of the disclosure, the heat transfer medium 74 does not generate a phase change within a working temperature range of the organism detection apparatus 100 (for example, from 50 degrees Celsius to less than 100 degrees Celsius). In another embodiment, the heat transfer medium 74 is a solid substance. In still another embodiment, the heat transfer medium 74 may be a liquid. In other embodiments, a material of the heat transfer medium 74 may also be a material of the reagent 54.

In detail, a relationship between the temperature change and the thermal resistance may be expressed as an equation (1) as follows, where Q is heat flux, R is thermal resistance of the heat transfer path, and ΔT is a difference in temperatures between two ends of the heat transfer path.

$$Q = \frac{\Delta T}{R} \qquad (1)$$

In addition, efficiency of heating may be expressed as an equation (2) as follows, where ΔT is an amount of the temperature change, Q is the heat flux, ρ is a density of a material, V is a volume of the material, Cp is a specific heat at constant pressure of the material, and t is time.

$$\int \Delta T dt = \int \frac{Q}{\rho V C p} dt \qquad (2)$$

It may be seen that ρVCp (that is, the heat capacity of the material) affects a temperature change slope, and the thermal resistance R affects temperature gradient. That is, the heat transfer medium 74 and the reagent 54 will have a same temperature change slope when the heat capacity of the heat transfer medium 74 is, as described above, equal to the heat capacity of the reagent 54. On the other hand, the reagent 54 and the thermal conductive structure 110 are separated by the test tube 52, therefore a thermal resistance (hereinafter referred to as a first thermal resistance) between the heat source 120 and the reagent 54 includes a material thermal resistance of the test tube 52, a contact thermal resistance between the test tube 52 and the thermal conductive structure, and a material thermal resistance of the carrier structure 110. The first thermal resistance is different from a thermal resistance between the heat source 120 and the heat transfer medium 74 (hereinafter referred to as a second thermal resistance), which includes a contact thermal resistance between the heat transfer medium 74 and the carrier structure 110 and the material thermal resistance of the carrier structure 110. Therefore, the first thermal resistance between the heat source 120 and the reagent 54 of the first reagent medium 50 may be different from the second thermal resistance between the heat source 120 and the temperature sensor 144B, and the difference in the thermal resistance generates a temperature difference constant.

Moreover, in a temperature sensing module 140B (shown in FIG. 11) of the embodiment, the processing unit 146B, after receiving a sensing signal from the temperature sensor 144B, according to the equation (1), may estimate a corresponding temperature difference constant from a wattage of the heat source 120 and the difference between the first thermal resistance and the second thermal resistance, and compensate a temperature sensed by the temperature sensor 144B according to the temperature difference constant, thereby deducing a temperature of the first reagent medium 50. In addition, since the heat transfer medium 74 is added to the carrier structure 110 in the embodiment, the heat transfer medium 74 absorbs a portion of the heat energy provided by the heat source 120, therefore the heat capacity of the heat transfer medium 74 needs to be taken into consideration when setting the wattage of the heat source 120, so as to prevent affecting the heating of each of the first reagent mediums 50 by the heat source 120 due to the addition of the heat transfer medium 74.

Figure 12:
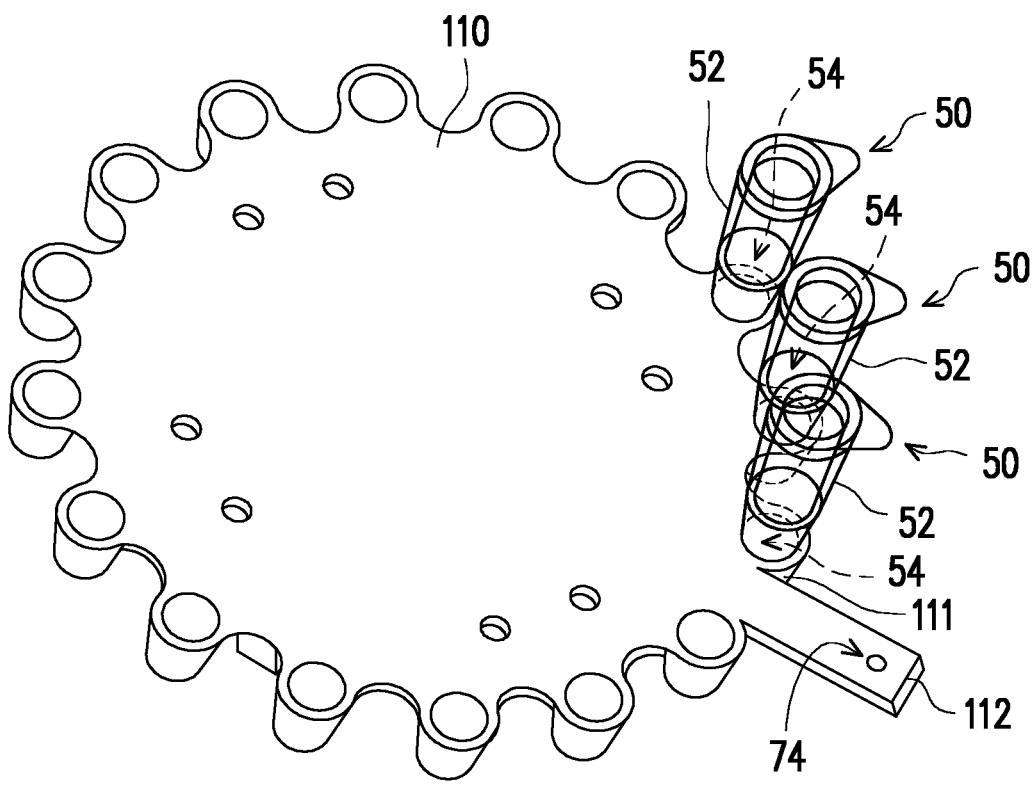
FIG. 12 is a perspective view of some of the components of a detection apparatus according to yet another embodiment of the disclosure.
Figure 13:
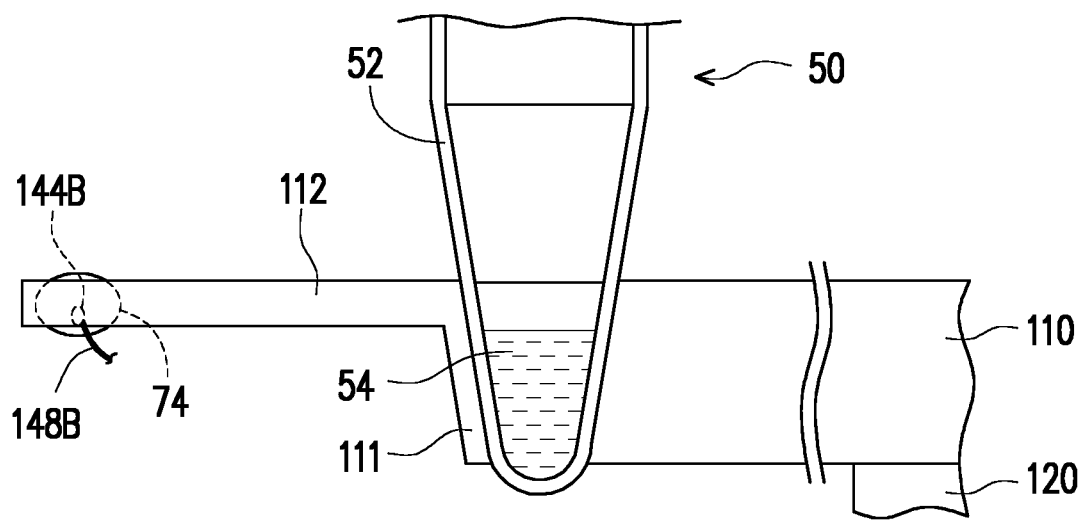
FIG. 13 shows some of the components of the temperature sensing module in FIG. 12.

FIG. 12 is a perspective view of some of the components of a detection apparatus according to yet another embodiment of the disclosure. FIG. 13 shows some of the components of the temperature sensing module in FIG. 12. A difference between the embodiment shown in FIGS. 12 and 13 and the embodiment shown in FIGS. 9 and 10 is that the heat transfer medium 74 shown in FIGS. 12 and 13 is configured on an extension portion 112 extending from the carrier structure 110, enabling a distance between the heat source 120 and the heat transfer medium 74 to be greater than a distance between the heat source 120 and the first reagent medium 50. In this configuration, the second thermal resistance between the heat source 120 and the heat transfer medium 74 may be increased, which enables it to be equal to the first thermal resistance between the heat source 120 and the reagent 54. Thus, there is almost no temperature difference between the heat transfer medium 74 and the first reagent medium 50 due to the difference in the thermal resistances, and the temperature of the heat transfer medium 74 sensed by the temperature sensor 144B may be regarded as the temperature of the reagent 54.

Specifically, the first thermal resistance between the heat source 120 and the reagent 54 may be calculated from a heat transfer coefficient, a path length, and a cross-sectional area of each of the heat transfer mediums between the heat source 120 and the reagent 54 according to an equation (3) as follows, where R is the thermal resistance, x is a distance between the two ends of the heat transfer path, A is the cross-sectional area of the heat transfer path, and k is the heat transfer coefficient of the heat transfer medium. Then, in order to enable the second thermal resistance between the heat source 120 and the heat transfer medium 74 to be equal to the first thermal resistance between the heat source 120 and the reagent 54, when the heat transfer coefficient and the cross-sectional area of each of the heat transfer mediums between the heat source 120 and the heat transfer medium 74 are known, a required heat transfer path distance may be calculated according to the following equation (3), so as to determine a required length of the extension 112 accordingly, and configure the heat transfer medium 74 at an end of the extension 112.

$$R = \frac{x}{Ak} \quad (3)$$

Figure 14:
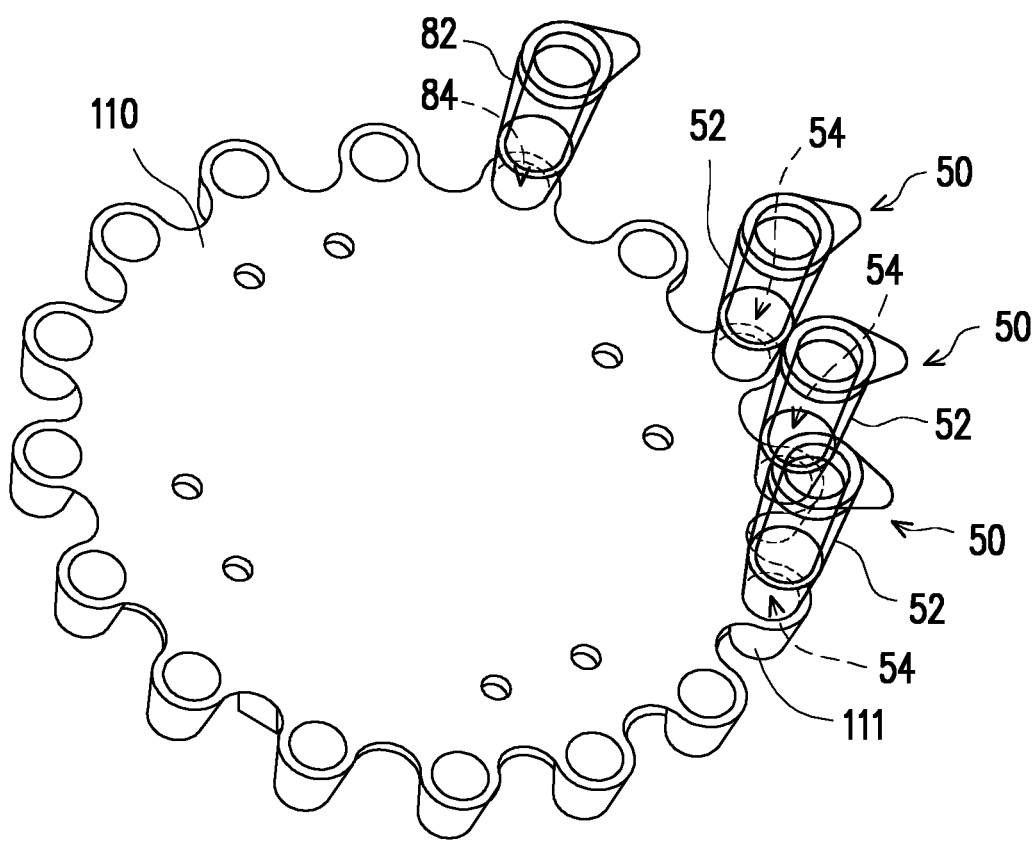
FIG. 14 is a perspective view of some of the components of a detection apparatus according to still another embodiment of the disclosure.
Figure 15:
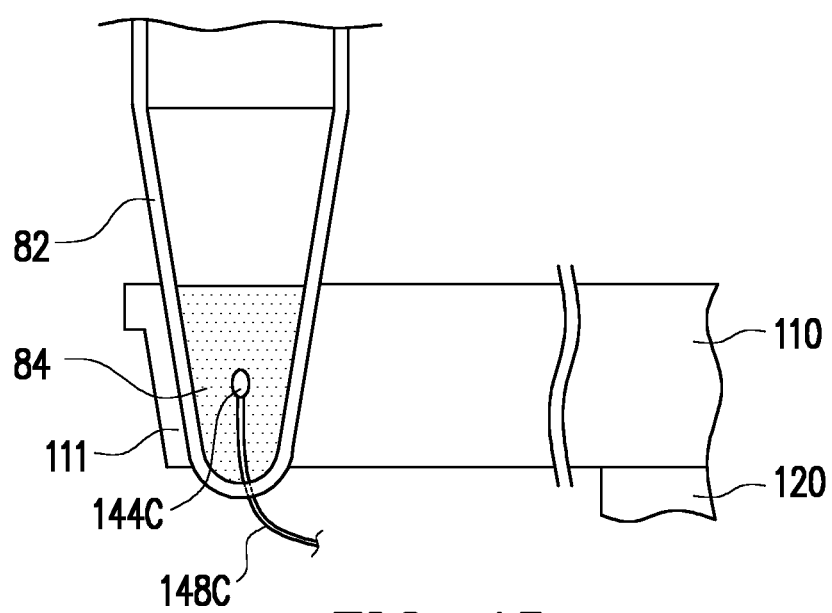
FIG. 15 shows some of the components of a temperature sensing module in FIG. 14.
Figure 16:
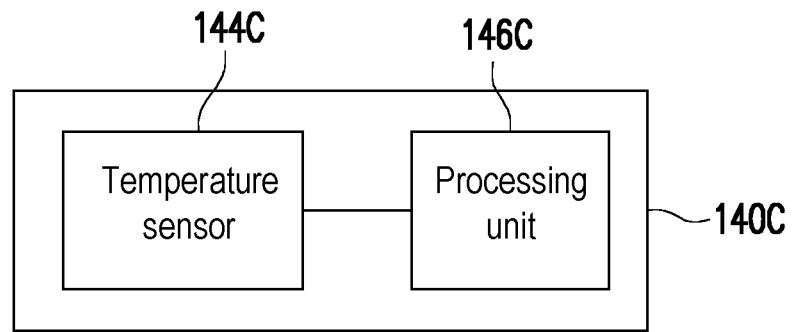
FIG. 16 is a schematic block diagram corresponding to the temperature sensing module in FIG. 15.

FIG. 14 is a perspective view of some of the components of a detection apparatus according to still another embodiment of the disclosure. FIG. 15 shows some of the components of a temperature sensing module in FIG. 14. FIG. 16 is a schematic block diagram corresponding to the temperature sensing module in FIG. 15. A difference between the embodiment shown in FIGS. 14 to 16 and the embodiment shown in FIGS. 6 to 8 is that a heat transfer medium 84 shown in FIGS. 14 to 16 is a non-reagent material and is accommodated in a test tube 82. A material and size specifications of the test tube 82 are same as those of the test tube 52. A material of the heat transfer medium 84 may be resin (such as nylon or polystyrene) or water, and its specific heat is different from that of the reagent 54. A heat capacity of the heat transfer medium 84 may be enabled to be approximately equal to the heat capacity (that is, the heat capacity preset value for detection) of the reagent 54 by controlling mass of the heat transfer medium 84. A temperature sensor 144C is located in the test tube 82. In this way, the temperature of the first reagent medium 50 may be accurately obtained through sensing of the temperature of the additional heat transfer medium 84 (the non-reagent medium) by the temperature sensor 144C. For example, if a target value of the reagent 54 is an aqueous solution with a volume V=20 µL=0.00002 m$^3$, and its density p is about 997 kg/m$^3$ and its specific heat at constant pressure Cp is about 4200 J/(kg·K), then a preset value of its heat capacity C is C=M*Cp=ρ*V*Cp=(997 kg/m$^3$)*(0.00002 m$^3$)*(4200 J/(kg·K))=83.748 J/K. A heat capacity preset value Cpreset of the heat transfer medium may be set to this target value of 83.748 J/K. After the material of the heat transfer medium is selected, its specific heat at constant pressure Cp may be determined, and its mass M may be calculated accordingly. If the density p may also be determined, the volume V may also be calculated. For example, if the reagent 54 is polystyrene and its specific heat Cp=1300 J/(kg·K) and its density p=1050 kg/m$^3$, then its volume V=0.000061 L=61 µL may be calculated. According to an embodiment of the disclosure, the volume or the mass of the heat transfer medium may be adjusted according to a target volume or a target mass of the reagent 54. Assuming that for the reagent 54, heat capacity=C1, mass=M1, density=ρ1, volume=V1, specific heat=Cp1, and for the heat transfer medium, heat capacity=C2, mass=M2, density=ρ2, volume=V2, specific heat=Cp2, then C1=C2, M1*Cp1=M2*Cp2, ρ1*V1*Cp1=ρ2*V2*Cp2. When it is known that the reagent 54 is a molten liquid and its specific heat Cp1=4200 J/(kg·K), its density ρ1=997 kg/m$^3$, and the heat transfer medium is polystyrene and its specific heat Cp1=1300 J/(kg·K) K), its density ρ1=1050 kg/m$^3$, then (4200)*(997)*V1=(1300)*(1050)*V2, and V2=3.07*V1 may be obtained by calculation. Therefore, when selection of the volume V1 of the reagent 54 is confirmed, the volume V2 of the heat transfer medium polystyrene may be 3.07 times of the volume V1. The calculation to determine the volume of the heat transfer medium is also applicable to the foregoing embodiment shown in FIGS. 9 to 13 and subsequent embodiment to be shown in FIGS. 17 to 20.

According to yet another embodiment of the disclosure, a temperature sensing module 140C is a replaceable module, in which multiple heat transfer mediums 84 with different thermal capacities may be designed to match with different heat capacity preset values for detection of the reagent 54, and be selected as required during actual usage. According to another embodiment of the disclosure, the temperature sensing module 140C is a replaceable module, in which multiple test tubes 82 or holding tubes 82 with different thermal resistances for matching are designed according to thermal resistance preset value of the different test tubes 52.

In detail, it may be seen from the equations (1) and (2) that ρVCp (that is, the heat capacity of the material) affects the temperature change slope, and the thermal resistance R affects the temperature gradient. That is, when the heat capacity of the heat transfer medium 84 is equal to the heat capacity of the reagent 54 as described above, the heat transfer medium 84 and the reagent 54 will have the same temperature change slope. On the other hand, since the reagent 54 and the heat transfer medium 84 are different from each other, the contact thermal resistance between the reagent 54 and the test tube 52 is different from the contact thermal resistance between the heat transfer medium 84 and the test tube 52. Therefore, the first thermal resistance between the heat source 120 and the reagent 54 of the first reagent medium 50 is different from the second thermal resistance between the heat source 120 and the temperature sensor 144C, and this difference in the thermal resistance generates a temperature difference constant.

Moreover, in the temperature sensing module 140C (shown in FIG. 16) of the embodiment, the processing unit 146C, after receiving the sensing signal from the temperature sensor 144C, according to the equation (1), may estimate the corresponding temperature difference constant from the wattage of the heat source 120 and the difference between the first thermal resistance and the second thermal resistance, and compensate the temperature sensed by the temperature sensor 144C according to the temperature difference constant, thereby deducing the temperature of the first reagent medium 50.

Figure 17:
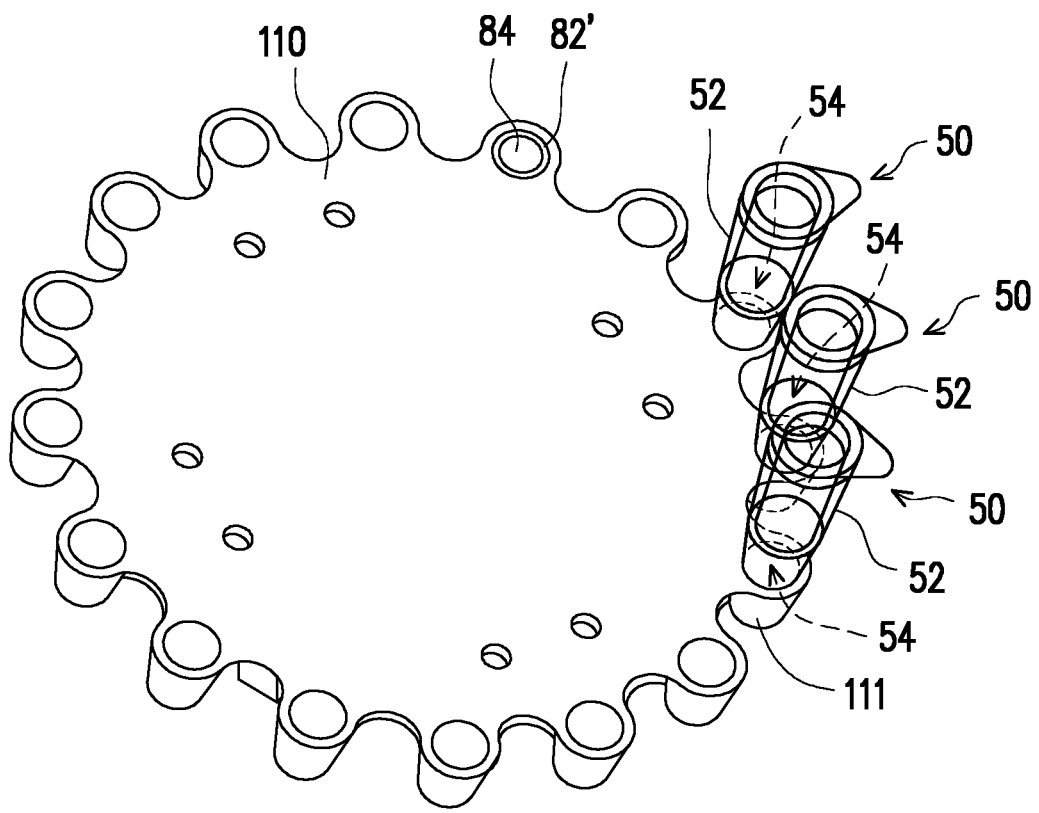
FIG. 17 is a perspective view of some of the components of a detection apparatus according to still yet another embodiment of the disclosure.
Figure 18:
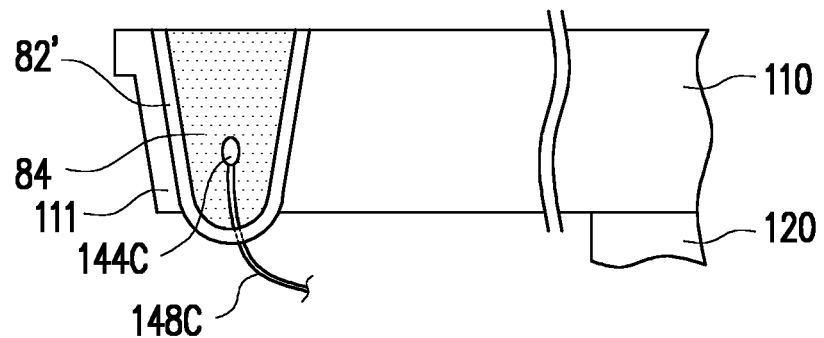
FIG. 18 shows some of the components of the temperature sensing module in FIG. 17.

FIG. 17 is a perspective view of some of the components of a detection apparatus according to still yet another embodiment of the disclosure. FIG. 18 shows some of the components of the temperature sensing module in FIG. 17. A difference between the embodiment shown in FIGS. 17 and 18 and the embodiment shown in FIGS. 14 and 15 is that a part of a test tube 82' shown in FIGS. 17 and 18 is truncated to enable its length to be less than a length of the test tube 52 of the first reagent medium 50. In this way, overall structure of a heat transfer medium 84' may be simplified. In the embodiment, although the test tube 82' is different from the test tube 52 of the first reagent medium 50, the truncated part of the test tube 82' has limited influence on overall heat absorption and heat transfer. In this way, the temperature sensor 144C in the test tube 82' accurately obtain the temperature of the first reagent medium 50 through sensing of temperature of the additional heat transfer medium 84'. Similar to the heat transfer medium 140C removable module of the embodiment shown in FIGS. 14 to 16, the heat transfer medium in the present embodiment may also be a removable module.

Figure 19:
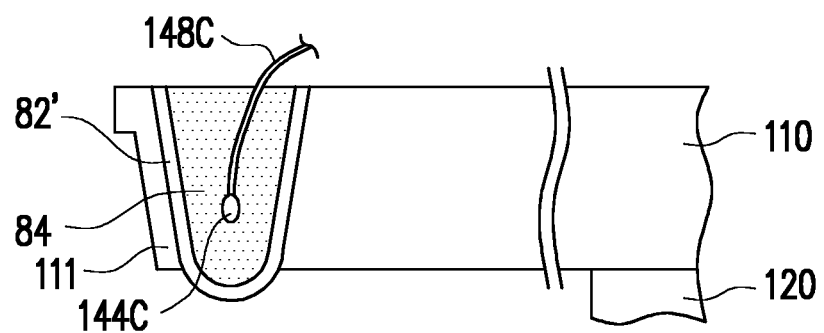
FIG. 19 shows an arrangement of the signal line which is different from that in FIG. 18.

In the embodiment shown in FIG. 18, a signal line 148C extends from a bottom end of the test tube 82 to outside of the test tube 82. However, the disclosure is not limited thereto. FIG. 19 shows an arrangement of the signal line which is different from that in FIG. 18. Since a part of test tube 82' is truncated, a top end of the heat transfer medium 84 is flushed with a top end of the test tube 82'. Therefore, the signal line 148C may be changed to extend from the top end of the test tube 82' to the outside of the test tube 82', as shown in FIG. 19.

Figure 20:
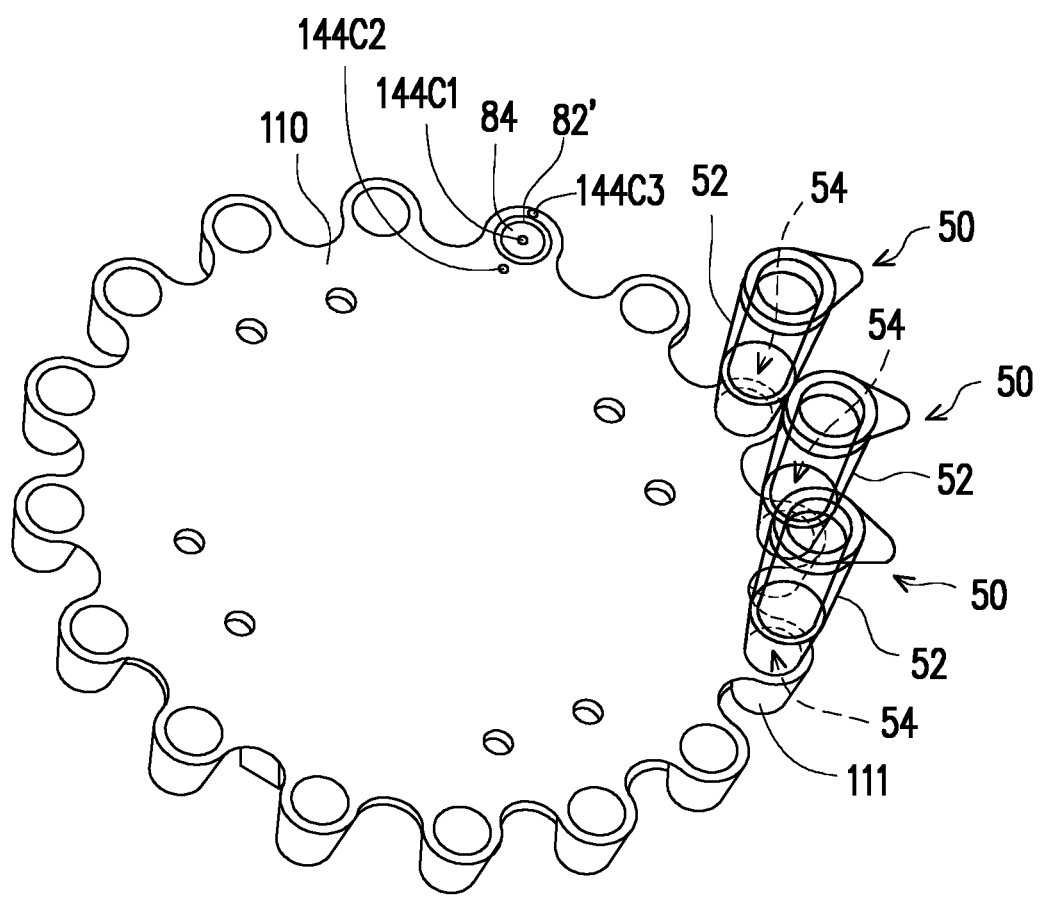
FIG. 20 shows arrangements of the position of the temperature sensor which are different from that in FIG. 18.

In addition, the disclosure does not limit a configuration position of the temperature sensor 144C. FIG. 20 shows arrangements of the position of the temperature sensor which are different from that in FIG. 18. In addition to configuring the temperature sensor 144C in the test tube 82' as shown in FIG. 18, the temperature sensor may also be configured on a top surface of the heat transfer medium 84 (labeled as a temperature sensor 144C1) as shown in FIG. 20, or the temperature sensor is configured on the carrier structure 110 and is located on an inner side the heat transfer medium 84 (labeled as a temperature sensor 144C2), or the temperature sensor is configured on the carrier structure 110 and located on an outer side of the heat transfer medium 84 (labeled as a temperature sensor 144C3).

The disclosure does not limit quantities of the temperature detection module and the additional heat transfer medium disposed in the above embodiments. Two or more of the temperature detection modules, the heat transfer mediums and the corresponding temperature sensors may be disposed, and an average value of the temperatures obtained by the multiple temperature sensors is regarded as the temperature of the reagent 54 in the first reagent medium 50. In addition, in the embodiments shown in FIGS. 6 to 20, multiple types of the temperature detection modules, the heat transfer mediums and the corresponding temperature sensors may be disposed on the carrier structure 110 in advance, and the multiple types of heat transfer mediums respectively have different heat capacity preset values for detection adapted for the reagent 54 having various heat capacity values, so as to allow the user to select a corresponding temperature sensed by the temperature sensor for temperature control according to requirements.

Furthermore, if the heat capacity values (that is, the heat capacity preset values for detection) of the multiple types of heat transfer medium disposed in advance are unable to directly correspond to the heat capacity value of the reagent 54 to be tested, a temperature of the reagent 54 may be estimated by interpolation or extrapolation according to a temperature sensed by the heat transfer medium of the temperature detection module and the corresponding temperature sensor disposed on the carrier structure, together with another temperature sensed by another heat transfer medium of another temperature detection module and another corresponding temperature sensor disposed on the carrier structure. FIG. 21 is a flowchart of a method for detecting a temperature of a specimen of an organism according to an embodiment of the disclosure. Specifically, as shown in FIG. 21, the carrier structure 110 carries the first reagent medium 50, a specimen, the temperature detection module 140, and another temperature detection module 140. The specimen is located in the first reagent medium 50, the temperature detection module 140 includes a heat transfer medium and the temperature sensor 144, and the another temperature detection module 140 includes another heat transfer medium and another temperature sensor 144. The heat capacity (i.e., the heat capacity preset value for detection) of the heat transfer medium is not equal to the heat capacity (i.e., the another heat capacity preset value for detection) of the another heat transfer medium (Step S1). A temperature of the corresponding heat transfer medium and another temperature of the another corresponding heat transfer medium are respectively sensed by the temperature sensor 144 and the another temperature sensor 144 (Step S2). The temperature of the first reagent medium 50 is obtained by calculation through interpolation or extrapolation according to the temperature of the heat transfer medium and the another temperature of the another heat transfer medium (Step S3).

In addition, multiple identical temperature detection modules may also be disposed for detection at the same time. That is, the temperature of the reagent 54 may be detected according to the temperature sensed by the heat transfer medium of the temperature detection module disposed on the carrier structure and the corresponding temperature sensor, together with the another temperature sensed by the another heat transfer medium of the another temperature detection module disposed on the carrier structure and the another corresponding temperature sensor, in which the heat capacity preset values for detection of the two heat transfer mediums are equal.

Figure 23:
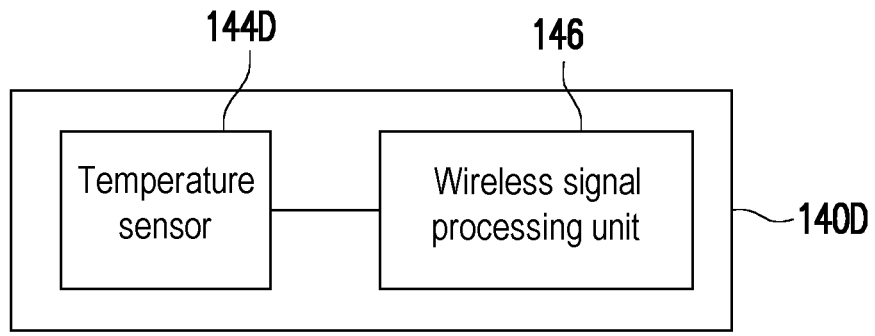
FIG. 23 is a schematic block diagram of a temperature sensing module in FIG. 22.

FIG. 22 is a partial schematic view of a detection apparatus according to yet still another embodiment of the disclosure. FIG. 23 is a schematic block diagram of a temperature sensing module in FIG. 22. With reference to FIGS. 22 and 23, a temperature detection module 140D of the embodiment includes a heat transfer medium 54, a temperature sensor 144D, and a wireless signal processing unit 146. In the embodiment, the heat transfer medium is the reagent 54 in one of the multiple test tubes 52. The temperature sensor 144D is accommodated in the corresponding test tube 52 and immersed in the reagent 54 to be adapted for sensing the temperature of the heat transfer medium (the reagent 54). The wireless signal processing unit 146 is configured to receive a wireless sensing signal from the temperature sensor 144D to obtain the temperature of the reagent 54 and the specimen.

In this configuration, the temperature sensor 144D directly measures the temperature of the reagent 54 in the test tube 52, and the scenario in which the sensed temperature does not match the actual temperature will not occur. In addition, the temperature sensor 144D transmits the sensing signal to the wireless signal processing unit 146 by wireless transmission, instead of using the signal line to transmit the sensing signal. Therefore, the structure of the temperature sensor 144D is extremely simple and convenient, and may prevent configuration of the signal line from affecting optical detection of the corresponding first reagent medium 50.

Figure 24:
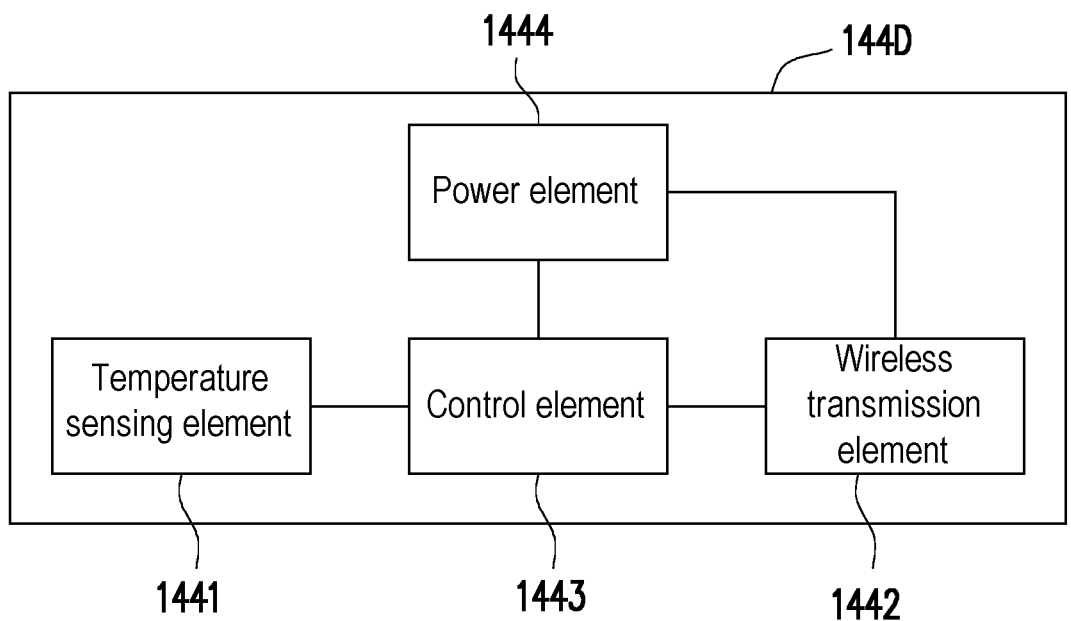
FIG. 24 is a schematic block diagram of the temperature sensor in FIG. 23.

FIG. 24 is a schematic block diagram of the temperature sensor in FIG. 23. In more detail, the temperature sensor 144D may include a temperature sensing element 1441, a wireless transmission element 1442, a control element 1443, and a power element 1444. The temperature sensing element 1441 may be a thermocouple, a thermal diode, a thermistor, etc., which may convert a temperature of an environment in which the sensor is located into an electrical signal. The control element 1443 is configured to convert physical quantity of the electrical signal from the temperature sensing element 1441 into the temperature information, and transmit it to the wireless signal processing unit 146 (shown in FIG. 23) through the wireless transmission element 1442. The power element 1444 may be a battery element, a wireless charging element, or a radio frequency element, configured to provide power required by the temperature sensing element 1441.

In all of the above embodiments, the factors related to the accuracy of the temperature measurement include at least whether the measured heat transfer medium and the first reagent medium have approximately the same, equivalent or similar heat capacity, whether their thermal fields are approximately the same or similar, and whether their thermal resistances are approximately the same, equivalent or similar. In the embodiment shown in FIGS. 6 to 8, composition of the second reagent medium 142A is the same as that of the first reagent medium, and its position and configuration are the same as those of the first reagent medium, therefore approximately conforming to conditions of having equivalent heat capacity, the same thermal field and equivalent thermal resistance, and can have good accuracy in temperature measurement. In the embodiment shown in FIGS. 9 to 11, although composition of the heat transfer medium 74 is different from that of the reagent 54, the heat transfer medium 74 has the same heat capacity as the reagent 54 by controlling its material type and mass, therefore approximately conforming to the condition of having equivalent heat capacity. A temperature measurement value can be compensated according to the temperature difference constant related to a difference between the two thermal resistances, and the accuracy of the temperature measurement is still better than the conventional measurement manner in which the temperature sensing element is simply embedded in the thermal conductive structure. In the embodiment shown in FIGS. 12 and 13, although the composition of the heat transfer medium 74 is different from that of the reagent 54, the heat transfer medium 74 has the same heat capacity as the reagent 54 by controlling its material type and mass, therefore approximately conforming to the condition of having equivalent heat capacity. In addition, the difference in the thermal resistances of the heat transfer medium 74 and the reagent 54 is compensated by increasing the distance between the heat transfer medium 74 and the heat source, so as to conform to the condition of having equivalent thermal resistance, and the accuracy of the temperature measurement is still better than the conventional measurement manner in which the temperature sensing element is simply embedded in the thermal conductive structure. In the embodiment shown in FIGS. 14 to 16 and the embodiment shown in FIGS. 17 to 19, although composition of the heat transfer medium 84 is different from that of the reagent 54, the heat transfer medium 84 has the same heat capacity as the reagent 54 by controlling its material type and mass, therefore approximately conforming to the condition of having equivalent heat capacity. In addition, its position and configuration are the same/similar to that of the reagent 54, therefore approximately conforming to the conditions of having equivalent heat capacity, the same/similar thermal field, and equivalent thermal resistance, and can have good accuracy in the temperature measurement. In the implementation manner corresponding to the temperature sensor 144C1 in the embodiment shown in FIG. 20, although the composition of the heat transfer medium 84 is different from that of the reagent 54, the heat transfer medium 84 has the same heat capacity as the reagent 54 by controlling its material type and mass, therefore approximately conforming to the condition of having equivalent heat capacity. In addition, its position and configuration are the same/similar to that of the reagent 54, therefore approximately conforming to the conditions of having equivalent heat capacity, the same/similar thermal field, and equivalent thermal resistance, and can have good accuracy in the temperature measurement. In the implementation manner corresponding to the temperature sensors 144C2 and 144C3 in the embodiment shown in FIG. 20, although the composition of the heat transfer medium 84 is different from that of the reagent 54, the heat capacity is the same as that of the reagent 54 by controlling its material type and mass, therefore approximately conforming to the condition of having equivalent heat capacity. In addition, its position and configuration are the same/similar to that of the reagent 54, therefore approximately conforming to the conditions of having equivalent heat capacity and equivalent thermal resistance. However, its temperature sensors 144C2 and 144C3 are configured on the inner side or the outer side of the heat transfer medium 84, causing the thermal field at the temperature sensing position to be relatively uneven, but the accuracy of the temperature measurement is still better than the conventional measurement manner in which the temperature sensing element in simply embedded in the thermal conductive structure. For the embodiment shown in FIG. 21, the position and configuration of the heat transfer medium are the same as that of the reagent, therefore conforming to the condition of having equivalent thermal resistance. Although the temperature of the reagent is estimated by the temperature measurement values of the at least two heat transfer mediums with thermal capacities different from that of the reagent, which does not conform to the condition of having equivalent heat capacity, the accuracy of the temperature measurement is still better than the conventional measurement manner in which the temperature sensing element in simply embedded in the thermal conductive structure. In the embodiment shown in FIGS. 22 and 23, the heat transfer medium is the reagent 54 itself, therefore conforming to the conditions of equivalent heat capacity, the same thermal field, and equivalent thermal resistance, and can have good accuracy in the temperature measurement.

Although the disclosure has been disclosed in the above embodiments, the embodiments are not intended to limit the disclosure. It will be apparent to persons skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A detection apparatus for performing polymerase chain reaction (PCR) testing, comprising:
    a carrier structure; and
    a temperature detection module, disposed on the carrier structure, wherein the temperature detection module comprises a heat transfer medium and a temperature sensor, the heat transfer medium does not contain a specimen, a heat capacity of the heat transfer medium is equal to a heat capacity preset value for detection, and the temperature sensor is disposed on the heat transfer medium to sense a temperature of the heat transfer medium while performing PCR testing,
    wherein the carrier structure further comprises an extension portion, and the heat transfer medium is disposed on the extension portion,
    wherein the carrier structure further comprises a plurality of sockets, the extension portion is extended away from the sockets, a plurality of test tubes are used to dispose on the sockets.

2. The detection apparatus according to claim 1, wherein the heat transfer medium does not generate a phase change within a working temperature range.

3. The detection apparatus according to claim 1, wherein the temperature detection module is a replaceable temperature detection module.

4. The detection apparatus according to claim 1, further comprising:
    another temperature detection module, disposed on the carrier structure, wherein the another temperature detection module comprises another heat transfer medium and another temperature sensor, the another heat transfer medium does not contain a specimen, a heat capacity of the another heat transfer medium is equal to another heat capacity preset value for detection, and the another temperature sensor is disposed in the another heat transfer medium and to sense another temperature of the another heat transfer medium while performing PCR testing.

5. The detection apparatus according to claim 4, wherein the another heat capacity preset value for detection is equal to the heat capacity preset value for detection.

6. The detection apparatus according to claim 4, wherein the another heat capacity preset value for detection is not equal to the heat capacity preset value for detection.

* * * * *